US006857324B2

(12) United States Patent
Sato et al.

(10) Patent No.: US 6,857,324 B2
(45) Date of Patent: Feb. 22, 2005

(54) METHOD AND APPARATUS FOR MEASURING CONCENTRATIONS OF COMPONENTS OF FLUID

(75) Inventors: Tetsuya Sato, Tokyo (JP); Shang-Qian Wu, Tokyo (JP); Tetsuya Kimijima, Tokyo (JP)

(73) Assignee: Nippon Sanso Corporation, Tokyo (JP)

( * ) Notice: Subject to any disclaimer, the term of this patent is extended or adjusted under 35 U.S.C. 154(b) by 0 days.

(21) Appl. No.: 10/413,964

(22) Filed: Apr. 14, 2003

(65) Prior Publication Data

US 2003/0172723 A1 Sep. 18, 2003

Related U.S. Application Data

(62) Division of application No. 10/108,073, filed on Mar. 26, 2002.

(30) Foreign Application Priority Data

Sep. 6, 2001 (JP) ........................................ 2001-270335

(51) Int. Cl.$^7$ .............................. G01F 1/42; G01F 1/68
(52) U.S. Cl. ................................. 73/861.61; 73/204.11; 73/861.63
(58) Field of Search .......................... 73/202.5, 204.11, 73/204.21, 861.01, 861.61, 861.63, 61.47, 61.41, 61.46, 61.76, 61.78, 23.2, 23.3, 54.14, 61.73, 64.46

(56) References Cited

U.S. PATENT DOCUMENTS

| | | | | | |
|---|---|---|---|---|---|
| 2,571,470 A | * | 10/1951 | Milligan | ...................... | 73/61.47 |
| 3,945,243 A | * | 3/1976 | Ouvrard | ...................... | 374/24 |
| 4,550,590 A | * | 11/1985 | Kesson | ...................... | 73/19.05 |
| 4,569,232 A | * | 2/1986 | Kim | ...................... | 73/861.04 |
| 4,583,396 A | * | 4/1986 | Hunt et al. | ................. | 73/61.73 |
| 4,813,270 A | * | 3/1989 | Baillie | ....................... | 73/861.04 |
| 5,663,491 A | * | 9/1997 | Beer | ......................... | 73/61.41 |
| 6,148,659 A | * | 11/2000 | Traina | ........................ | 73/25.01 |
| 6,395,557 B1 | * | 5/2002 | Fouillet et al. | ............. | 436/148 |
| 6,536,262 B2 | * | 3/2003 | Baldauf et al. | ............ | 73/61.47 |

FOREIGN PATENT DOCUMENTS

| | | | | | |
|---|---|---|---|---|---|
| JP | 60129618 A | * | 7/1985 | ............. | G01F/1/00 |
| JP | 60129642 A | * | 7/1985 | ............. | G01N/7/00 |

\* cited by examiner

*Primary Examiner*—Charles D. Garber
(74) *Attorney, Agent, or Firm*—J.C. Patents (57) ABSTRACT

A method and an apparatus for measuring the concentrations of the components of a fluid are described, which can be used to measure the concentrations of the components continuously in real time and to monitor a high pressure gas, and is suitably used for in-line monitoring. In the method and the apparatus, a fluid sample is conducted through a measuring tube, wherein the measuring tube has a small aperture with a constant diameter in a fluid flow path. The pressure difference (P1–P2) between the upstream and the downstream of the small aperture and the flow rate at the downstream of the small aperture are measured to determine the concentrations of the components of the fluid.

6 Claims, 14 Drawing Sheets

METHOD AND APPARATUS FOR MEASURING CONCENTRATIONS OF COMPONENTS OF FLUID

CROSS-REFERENCE TO RELATED APPLICATION

This application is a divisional application of, and claims the priority benefit of, U.S. application Ser. No. 10/108,073 filed on Mar. 26, 2002.

BACKGROUND OF THE INVENTION

1. Field of Invention

The present invention relates to a method and an apparatus for measuring the concentrations of the components of a fluid. More particularly, the present invention relates to a method and an apparatus capable of rapidly and continuously measuring the concentrations of the components of a fluid.

2. Description of Related Art

In various processes of gas production or semiconductor fabrication, it is quite important to be able to control the concentrations of the components of a gas/liquid fluid in real time with a low cost. For example, in a gas separation apparatus, the concentrations of the gas components at its outlet varies as the one at its inlet varies. Therefore those concentrations have to be measured continuously in order to adjust the conditions for gas separation and to control the concentrations of the components of the gas product. Similarly, the concentrations of the components of a fluid need to be measured continuously in other applications that requires controlling the concentrations of gas/liquid components. Particularly, in the field of semiconductor process, the performance of a semiconductor product is relatively dependent on the concentrations of impurities in a high-purity gas being used. If the high-purity gas is contaminated by undesired components or varies in its composition, the yield of the semiconductor products will be reduced significantly.

In the prior art, a component with a relatively high concentration in a gas are analyzed by using gas chromatography (GC) or non-dispersive infrared (NDIR) spectroscopy. However, the GC method can only perform non continuous measurement and can not be used for continuous measurement in real time. Moreover, since the GC method uses a separating column to separate each component of a gas sample, the gas sample to be measured has to be mixed with a carrier gas like helium (He) and therefore can not be reused after the measurement. Consequently, the so-called "in-line monitoring" can not be implemented by using the GC method.

On the other hand, the NDIR spectroscopy can be used for continuous monitoring in real time and is a method frequently used for in-line monitoring. However, since a window made from an IR-transparent material, such as quartz, has to be disposed on the cell of an IR spectrometer, the measuring apparatus for measuring a high-pressure gas is quite bulky. Moreover, since the components to be measured must be IR active, the IR method has the disadvantage that it can not be used to monitor the components IR inactive such as nitrogen ($N_2$) and oxygen ($O_2$), which easily leak into the cell and highly require to be monitored.

SUMMARY OF THE INVENTION

Accordingly, this invention provides a method and an apparatus capable of measuring the concentrations of the components of a fluid in real time and implementing in-line monitoring. The method and the apparatus can be used to measure a high-pressure gas or to measure the concentrations of various components in a fluid.

In a method for measuring the concentrations of the components of a fluid disclosed in this invention, a fluid sample is conducted through a measuring tube having a small aperture with a constant diameter in a fluid flow path. The pressure difference between the upstream and the downstream of the small aperture and the flow rate at the downstream of the small aperture are measured to determine the concentrations of the components of the fluid.

In another method for measuring the concentrations of the components of a fluid disclosed in this invention, the fluid sample is conducted through a measuring tube having a small aperture with a constant diameter in a fluid flow path. The pressure difference between the upstream and the downstream of the small aperture is controlled to be constant and the flow rate at the downstream of the small aperture is measured to determine the concentrations of the components of the fluid.

In the two methods of this invention mentioned above, at least one of the temperatures of the fluid sample, the measuring tube and the circumstance of the measuring tube can be measured to correct the concentrations of the components just being determined. Besides, it is also feasible to control at least one of the temperatures of the fluid sample, the measuring tube and the circumstance of the measuring tube to be constant.

An apparatus for measuring the concentrations of the components of a fluid disclosed in this invention comprises a measuring tube, a differential pressure gauge, a flow meter and a calculating device. The measuring tube has a small aperture with a constant diameter is in a fluid flow path. The differential pressure gauge is used for measuring the pressure difference between the upstream and the downstream of the small aperture. The flow meter is used for measuring the flow rate of the fluid at the downstream of the small aperture. The calculating device is used to calculate the concentrations of the components of the fluid from the pressure difference and the flow rate being measured.

Another apparatus for measuring the concentrations of the components of a fluid described in this invention comprises a measuring tube, a differential pressure controller, a flow meter and a calculating device. The measuring tube has a small aperture with a constant diameter in a fluid flow path. The differential pressure controller is used for controlling the pressure difference between the upstream and the downstream of the small aperture to be constant. The flow meter is used for measuring the flow rate of the fluid at the downstream of the small aperture. The calculating device is used for calculating the concentration of the component of the fluid sample from the constant pressure difference and the flow rate being measured.

The two apparatus of this invention each may further comprises a temperature measuring device for measuring at least one of the temperatures of the fluid sample, the measuring tube and the circumstance of the measuring tube, while the calculating device is capable of correcting the concentrations of the components based on the temperature being measured. Besides, the apparatus may include a temperature controller for controlling at least one of the temperatures of the fluid sample, the measuring tube and the circumstance of the measuring tube.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings, FIG. 1 schematically illustrates a cross-sectional view of a measuring tube that has a small orifice-type aperture with a constant diameter in a fluid flow path in order to explain the rudiments of this invention.

DESCRIPTION OF THE PREFERRED EMBODIMENTS

Figure 1:
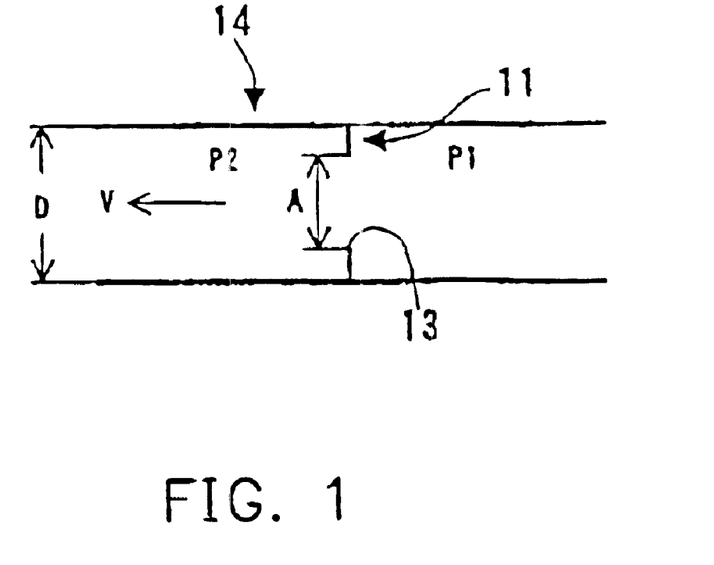
Figure 2:
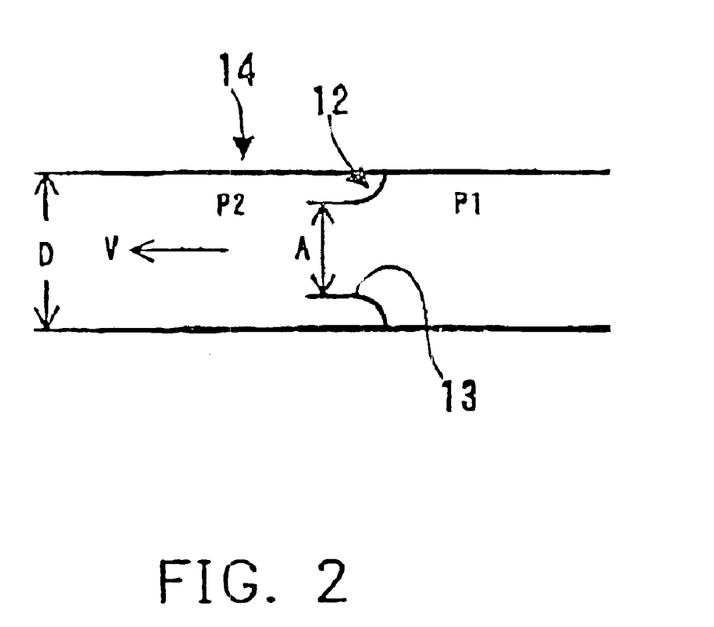
FIG. 2 schematically illustrates a cross-sectional view of a measuring tube that has a small nozzle-type aperture with a constant diameter in a fluid flow path.
Figure 3:
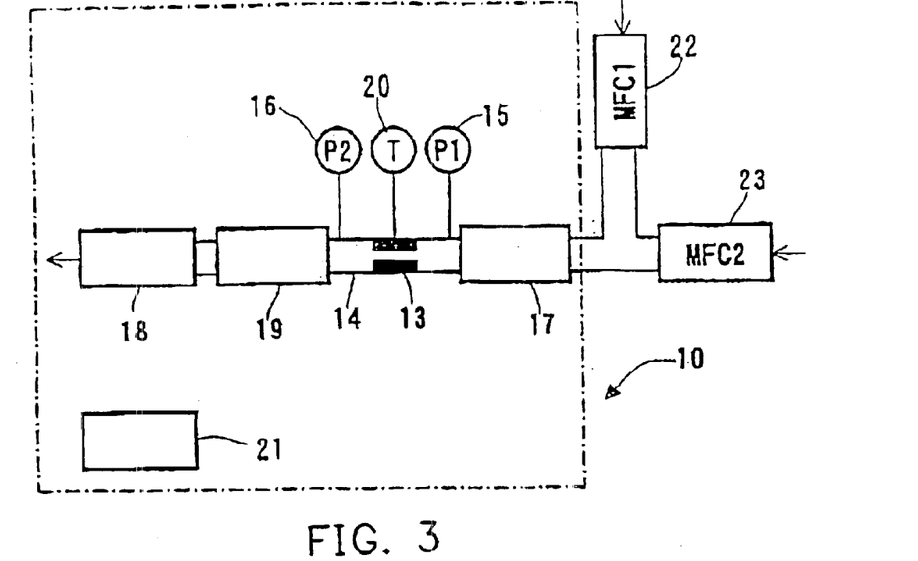
FIG. 3 illustrates the configuration of a measuring apparatus according to an embodiment of this invention.

Refer to FIG. 1 and FIG. 2 to further understand the rudiments of this invention. FIG. 1 schematically illustrates a cross-sectional view of a measuring tube that has a small orifice-type aperture with a constant diameter in a fluid flow path. FIG. 2 schematically illustrates a cross-sectional view of a measuring tube that has a small nozzle-type aperture with a constant diameter in a fluid flow path.

As shown in FIG. 1 and FIG. 2, when a fluid flows through a measuring tube 14 that has a small aperture consisting of an orifice 11 or a nozzle 12 with an aperture area A being quite small as compared with the diameter D of the measuring tube 14. The flow rate of the fluid can be determined from the pressure difference between the upstream and the downstream of the small aperture 13. Namely, when the fluid is a non-compressive and vortex-free flow, the equation below can be derived from Bernoulli's theorem:

$$v = \{2(P1-P2)/d\}^{1/2}$$

wherein P1 and P2 are the fluid pressures at the upstream and the downstream of the small aperture 13, respectively, v is the flow velocity of the fluid at the downstream and d is the density of the fluid.

Moreover, the flow rate Q of the fluid is a product of the velocity v, the aperture area A of the small aperture 13 and a flow coefficient c for correcting the flow velocity based on the compressibility and the viscosity of the fluid:

$$Q = cAv = cA\{2(P1-P2)/d\}^{1/2}$$

The flow coefficient c varies with an aperture ratio m that is expressed by $m = A/(\pi D^2/4)$. However, when a nozzle is used in the measure tube 14, the fluid will not be compressed substantially so that the flow coefficient c will approach to 1.

It is known from the equation above that when the density of the fluid is constant, the flow rate Q can be derived from the pressure difference (P1–P2) and the area A of the small aperture 13. However, when the fluid is mixed with a component having a density quite different from that of the original fluid, the density of the whole fluid is changed so that the flow rate will change remarkably even if the pressure difference and the aperture area A are both unchanged. Therefore, based on the pressure difference and the fluid being set, the concentration of the component mixed in the fluid can be determined by the correlation data of the flow rate and the mixed concentration of the component. However, the method may also be conducted without controlling the pressure difference, wherein the pressure difference is monitored continuously and the flow rate is corrected accordingly, while the concentration of the component is determined from the corrected flow rate. Moreover, in order to measure the concentration precisely, the temperature of the fluid may be controlled to be constant. Alternatively, the temperature of the fluid may be monitored continuously and the flow rate is corrected accordingly, while the concentration of the component is determined from the corrected flow rate similarly.

In principle, since the pressure difference and the flow rate of the fluid are the basis of the measurement, the concentration of a component can be measured continuously in real time. Since the sensitivity in the concentration measurement is relatively dependent on the density of the fluid, the method is preferably used for measuring the fluid that consists of two components with quite different densities (or different molecular weights in a gas fluid). Moreover, the concentrations of IR inactive compounds, such as oxygen ($O_2$), nitrogen ($N_2$), helium (He), argon (Ar) and krypton (Kr), can also be measured. Furthermore, the method is preferably used to measure a high pressure fluid if only the parts in the apparatus are designed for use in a high pressure condition, or to measure a corrosive fluid if only the parts are made from corrosion-resistant materials. Moreover, since the fluid sample will not be contaminated and will not decompose or react with anything during the measurement, the fluid sample can be reused in the process by using this method. Therefore, this method is more preferably used for in-line monitoring.

Refer to FIGS. 3~8, which illustrate the configurations of the measuring apparatuses according to various embodiments of this invention. The apparatus 10 for measuring the concentrations of the components of a fluid comprises a measuring tube 14, an upstream-side pressure gauge (P1) 15 and a downstream-side pressure gauge (P2) 16, an upstream-side pressure controller 17 and a downstream-side pressure controller 18, a flow meter 19, a temperature measuring device 20 and a calculating device (computer) 21. The measuring tube 14 has a small aperture 13 with a constant diameter in a fluid flow path. The upstream-side pressure gauge 15 and the downstream-side pressure gauge 16 are used for calculating the pressure difference (P1−P2) between the upstream and the downstream of the small aperture 13. The upstream-side pressure controller 17 and the downstream-side pressure controller 18 are used for controlling the pressures at the upstream and the downstream of the small aperture 13, respectively. The flow meter 19 is used for measuring the flow rate of the fluid at the downstream of the small aperture 13. The temperature measuring device 20 is used to measure the temperature of the circumstance of the small aperture 13. The calculating device (computer) 21 is capable of calculating the concentration of the component by using the measuring results obtained with the measurers 15, 16, 19 and 20 or the controlled values that are set with the controllers 17 and 18 as the input data.

Moreover, the embodiments of this invention illustrated by FIG. 3~7 also describe some exemplary configurations for evaluating the performance of the apparatus 10 for measuring the concentrations of the components of a fluid. In each configuration, a first flow controller (MFC1) 22 and a second flow controller (MFC2) 23 are set at the upstream of the apparatus 10 to vary the mixing ratio of the two components in the fluid supplied to the measuring tube 14.

Before the measurement of the concentrations of the components in the fluid sample to be measured, two components that are the same as those of the fluid sample to be measured are mixed with their concentrations being controlled moderately by the first flow controller 22 and the second flow controller 23. The mixture is then conducted into the measuring tube 14 with the pressure difference between the upstream and the downstream of the small aperture 13 being controlled by using the upstream-side pressure controller 17 and the downstream-side pressure controller 18. As mentioned before, the flow rate of the fluid flowing in the measuring tube 14 and passing through the small aperture 13 varies with the density of the fluid (or the mean molecular weight of a gas fluid). Therefore, when the concentrations of the components are varied with the first flow controller 22 and the second flow controller 23, the flow rate measured with the flow meter 19 is changed. Therefore, a calibration curve can be made showing the correlation between the concentrations of the components and the flow rate of the fluid. Consequently, when a fluid sample consists of the two components with unknown concentrations, the fluid sample can be conducted through the measuring tube 14, thereby the concentrations of the components can be determined from the flow rate being measured according to the calibration curve. Moreover, when the concentrations of the components of the fluid sample also change with time, the concentrations can also be traced continuously. Furthermore, when the flow rate of the supplied fluid is large, a bypass line can be set at a proper position to branch the fluid sample such that only a moderate amount of the fluid is supplied into the measuring tube 14.

The small aperture 13 in the measuring tube 14 needs to have a high resistance to the pressure of the fluid and can be of any type if only an opening can be formed with a constant diameter during the measurement. The diameter of the small aperture 13 can be fixed or be variable, including the above-mentioned orifice 13a (see FIG. 4), a capillary tube and a needle valve 13b (see FIG. 5), etc. The two pressure gauges 15 and 16 can be of any type if only they are capable of measuring the pressure of the fluid for the determination of the pressure difference. Besides, a differential pressure gauge 15a (See FIG. 6) can be used to measure the pressures at the upstream and the downstream of the small aperture 13 simultaneously. Moreover, when the pressure at the upstream side or at the downstream side can be kept constant because of some specific using conditions or other factors, the pressure gauge at the side where the pressure is constant can be saved. Furthermore, when the pressures at the upstream side and at the downstream side can be both kept constant and the pressure difference is therefore constant, the two pressure gauges can be both saved.

Figure 7:
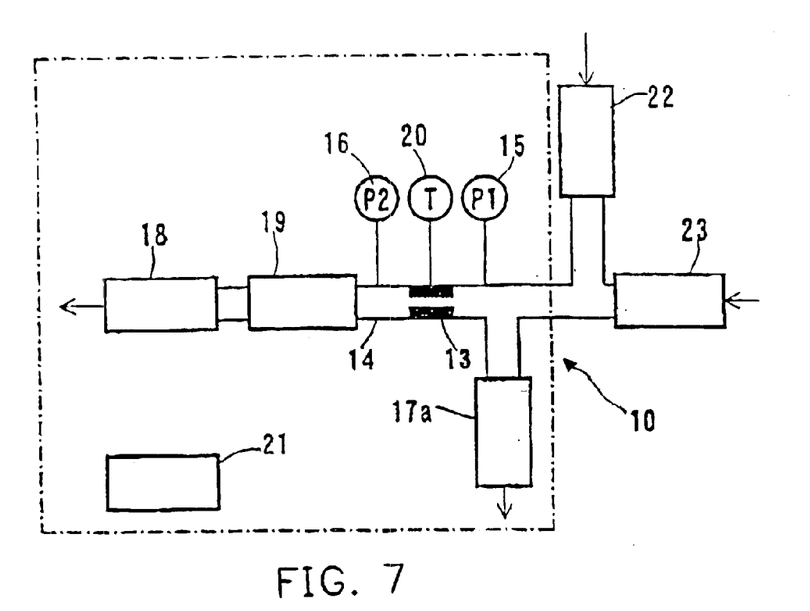
FIG. 7 illustrates the configuration of a measuring apparatus according to still another embodiment of this invention.

The pressure controllers 17 and 18 can also be of any type if only they can be used to well control the fluid pressure in the measuring tube 14. Since the pressure difference can be controlled to be constant, the concentrations of the fluid components can be determined accurately by only measuring the flow rate of the fluid at the downstream of the small aperture 13. Moreover, when the pressure at the upstream side or at the downstream side can be kept close to a constant within an acceptable range because of some specific using conditions or other factors, the pressure controller 17 or 18 at the side where the pressure is constant can be saved. In addition, when the concentrations of the fluid components are determined by the flow rate at the downstream of the small aperture 13 and the pressure difference (P1–P2) over the small aperture 13, the pressure controllers 17 and 18 can be both saved. Besides, the upstream-side pressure controller 17 can be replaced by a back pressure regulator 17a, which is illustrated in FIG. 7, to increase the efficiency of the concentration measurement.

The flow meter 19 can be of any type if only it can be used to accurately measure the flow rate of the fluid being monitored. Depending on the species of the fluid being measured, the flow meter 10 can be a mass flow meter (MFM), a soap film flow meter, a float flow meter, a rotary impeller flow meter, an Oval Gear flow meter, a Karman vortex flow sensor, an ultrasonic flow meter, a Coriolis flow meter or a sonic nozzle flow meter, etc. Among them, the mass flow meter has a high-speed responsibility and can be used for continuous measurement, and is therefore one of the most preferable flow meters that are suitably used in this invention.

Moreover, in a semiconductor fabricating apparatus or the like, it is preferable to use a mass flow meter that will not cause any internal contamination and have an excellent resistance to corrosion effects, so that the fluid sample will not be contaminated. Furthermore, when the thermal conductivities of the components are quite different as well as their densities, a mass flow meter that measures a flow rate by detecting thermal conductivity can be used to improve the measuring sensitivity synergistically and is therefore more preferable among the commercially available mass flow meters. For example, a mass flow meter is particularly effective for measuring a gas mixture of two components with any one of the combinations marked by hollow circles "O" in Table 1 since the molecule with a larger molecular weight has a lower thermal conductivity in each marked combination.

TABLE 1

|  | He | Ar | Kr | $N_2$ | $H_2$ | CO | $CO_2$ | $CH_4$ |
|---|---|---|---|---|---|---|---|---|
| He |  |  |  | O |  |  |  |  |
| Ar |  |  |  | O | O | O |  | O |
| Kr |  |  |  | O | O | O | O | O |
| Xe |  |  |  | O | O | O | O | O |
| $N_2$ |  | O | O |  |  |  |  | O |
| $H_2$ | O | O | O |  |  |  |  |  |
| $O_2$ |  | O | O |  |  |  |  | O |
| CO |  | O | O |  |  |  |  | O |
| $CO_2$ |  |  | O |  |  |  |  |  |
| $AsH_3$ |  |  | O |  |  |  |  |  |
| $BF_3$ |  |  | O |  |  |  |  |  |
| $B_2H_6$ |  | O | O |  |  | O | O |  |
| $PH_3$ |  | O | O |  |  |  | O |  |
| $SiH_4$ |  | O | O |  |  |  | O |  |
| $WF_6$ |  |  |  |  |  |  |  |  |
| $Cl_2$ |  |  | O |  |  |  | O | O |
| HCl |  | O | O |  |  |  | O |  |
| $NH_3$ |  | O | O | O |  | O |  |  |
| $CF_4$ |  |  |  |  |  |  |  |  |
| $C_2F_6$ |  |  |  |  |  |  |  |  |
| $CH_4$ |  | O | O | O |  | O |  |  |
| $C_2H_6$ |  | O | O |  |  |  | O |  |
| $C_3H_8$ |  |  | O |  |  |  | O |  |
| NO |  | O | O |  |  |  |  | O |
| $N_2O$ |  |  | O |  |  |  | O |  |

Moreover, in many cases the temperature variation of the fluid or that of the pipeline will change the flow rate and thereby cause an error in the measurement of the concentrations. To solve the problem, a temperature measuring device 20 is used for continuously measuring the temperatures of the fluid sample, the region around the small aperture 13, the measuring tube 14 and the circumstance of the measuring tube 14 for correcting the flow rate output measured by using the flow meter 19. Thereby, the concentrations of the components in a fluid can be determined accurately even if the temperature changes with time. However, when the apparatus of this invention is used in a location in which the temperature little changes, such as a clean room, the temperature of the apparatus or that of the fluid sample will not change and the temperature measuring device 20 therefore can be saved. Moreover, the whole apparatus can be accommodated in a thermostat to keep the temperature of the fluid sample or that of the measuring tube 14 as a constant so that the concentrations can be measured accurately without the temperature measuring device 20.

In the concentration measuring process, the calculating device 21 mentioned before is used for collecting the output data of each measurer or controller and correct the results according to the measured temperature variation or the pressure variation. Therefore, even though the temperature or the pressure changes with time, the concentrations of the fluid components can be determined and output in real time.

Figure 4:
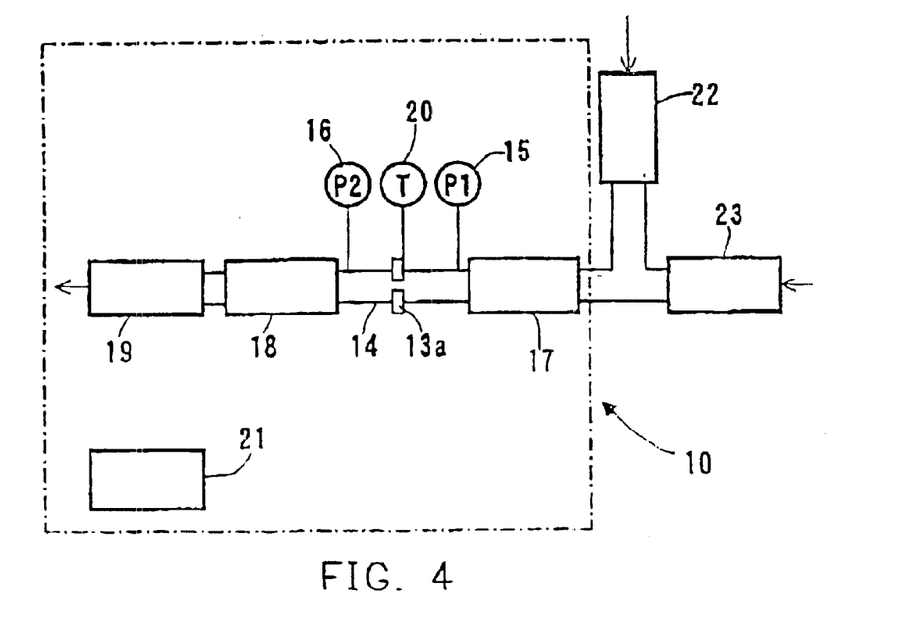
FIG. 4 illustrates the configuration of a measuring apparatus according to another embodiment of this invention.
Figure 5:
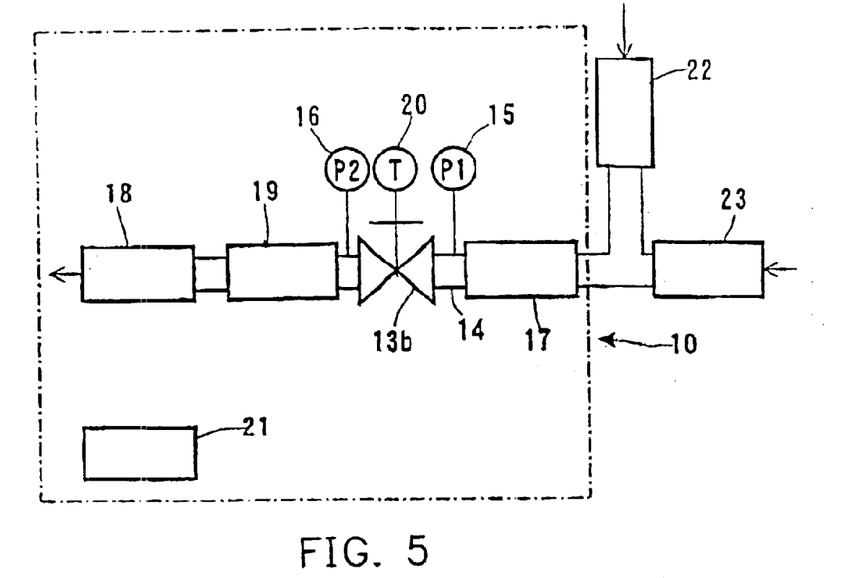
FIG. 5 illustrates the configuration of a measuring apparatus according to still another embodiment of this invention.
Figure 6:
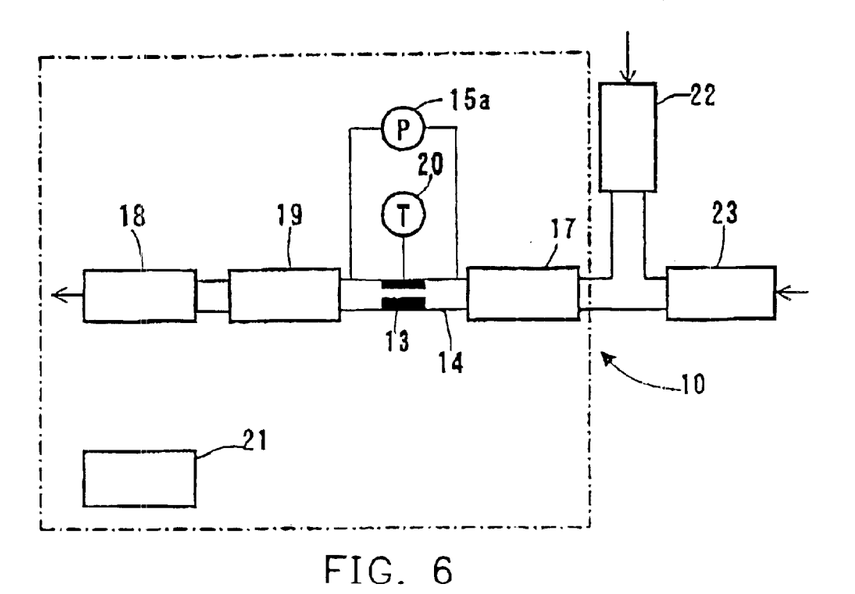
FIG. 6 illustrates the configuration of a measuring apparatus according to still another embodiment of this invention.

Moreover, the constituting parts of the apparatus disclosed in this invention, including the measuring tube 14 having a small aperture 13 with a constant diameter, the flow meter 19, the pressure gauge 15 and 16 and the temperature measuring device 20, etc., need not to be separated and can be used as an integrated part. Furthermore, as shown in FIG. 4, the downstream-side pressure controller 18 can be disposed at the upstream of the flow meter 19.

Moreover, except for a two-component fluid for which the concentration of each component can be determined exactly, the method and the apparatus of this invention can also be used to measure a fluid consisting of three or more components. In this situation, the total concentration of more than one trace components can be determined if only the sensitivity of each trace component in the fluid deviates from that of the matrix component by the same (±) sign. Accordingly, when a pure fluid is being controlled for the concentration of the impurity in it, the above-mentioned apparatus and method of this invention can be used to detect the impurities in the pure fluid even when a plurality of unknown components are possibly mixed into the pure fluid.

Figure 8:
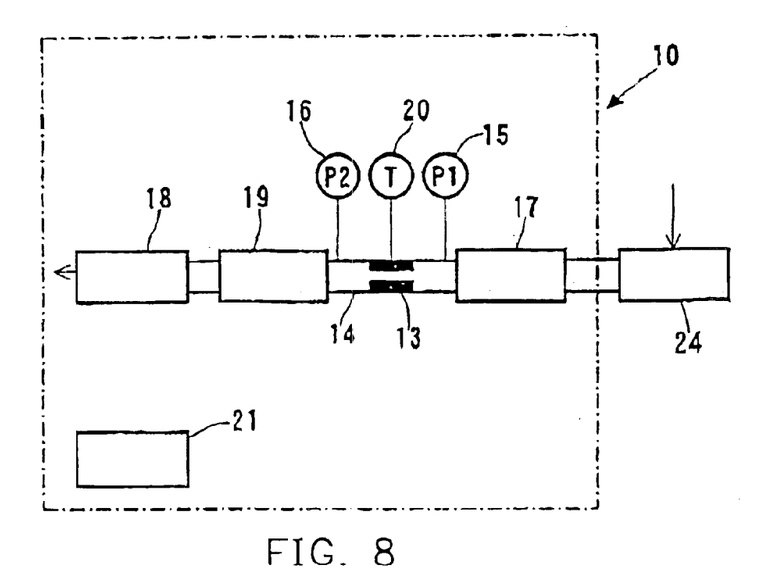
FIG. 8 illustrates the configuration of a measuring apparatus according to still another embodiment of this invention.

Furthermore, refer to FIG. 8, when a fluid sample that contains impurities comprising unknown materials is to be analyzed qualitatively, a separation column 24, such as a gas chromatograph or a liquid chromatograph, is disposed at the upstream of the measuring tube 14. The impurities in the fluid sample are separated from each other and then conducted into the measuring tube 14 in turn, so that the concentration of each component can be determined. The concentrations of multi components thus can be measured in spite that a continuous measurement can not be achieved.

EXAMPLE 1

Figure 9:
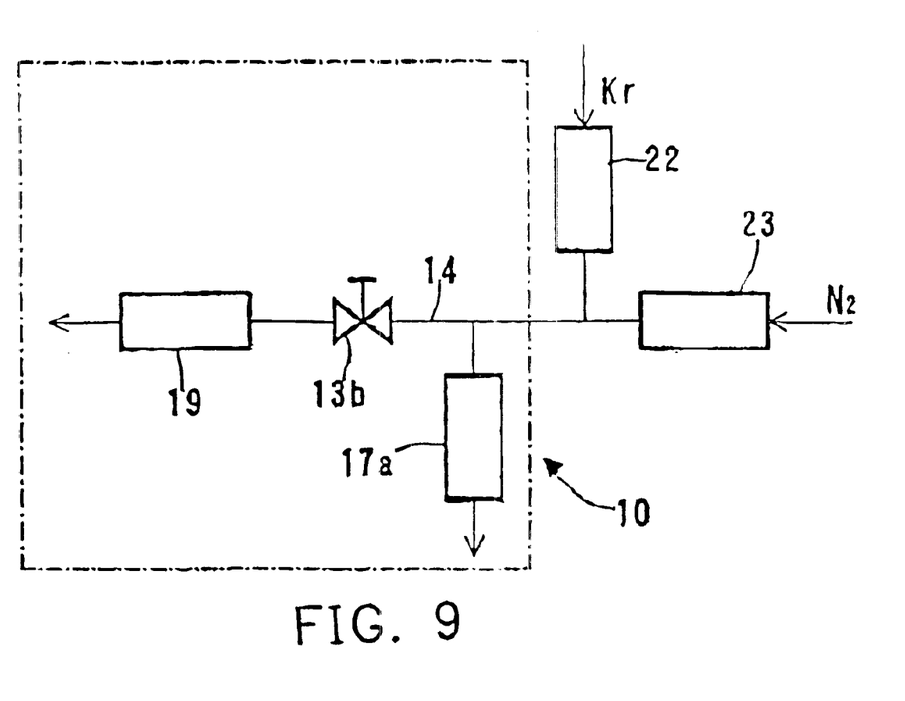
FIG. 9 illustrates the configuration of the experimental apparatus used in Example 1.

In this case, the experimental apparatus illustrated in FIG. 9 is used, wherein the measuring tube 14 includes a needle valve 13 (UCVIILM manufactured by MOTOYAMA ENG. WORKS, LTD.) therein. A first and a second flow controllers 22 and 23 for introducing krypton (Kr) gas and nitrogen ($N_2$) gas, respectively, are disposed at the upstream-side. A back-pressure regulator 17a (UR7340B by STEC) is disposed in the apparatus. A flow meter 19 (SEF4400 mass flow meter of thermal conductive-type by STEC) is disposed at the downstream side.

Figure 10:
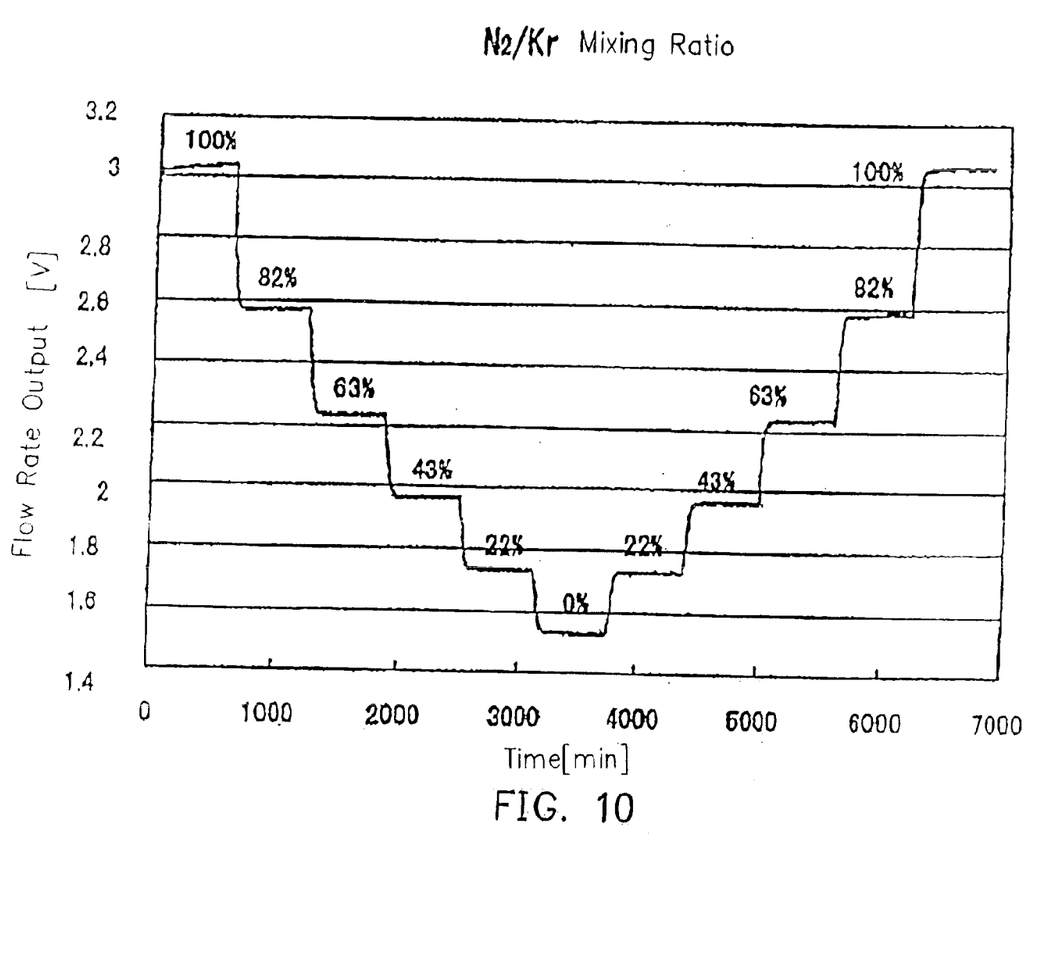
FIG. 10 plots the flow rate output measured with the flow meter with different mixing ratios of nitrogen and krypton ($N_2$/Kr)

The valve lift of the needle valve 13b is appropriately set and the fluid pressure is set to be 145 kPa by using the back pressure regulator 17a. The two flow controllers 22 and 23 are used to change the mixing ratio of krypton (Kr) and $N_2$, and each mixture with a specific mixing ratio is conducted through the needle valve 13b to be measured by using the flow meter 19. The correlation between the flow rate output measured with the flow meter 19 and the mixing ratio of krypton and nitrogen ($N_2$/Kr) is shown in FIG. 10.

EXAMPLE 2

Figure 11:
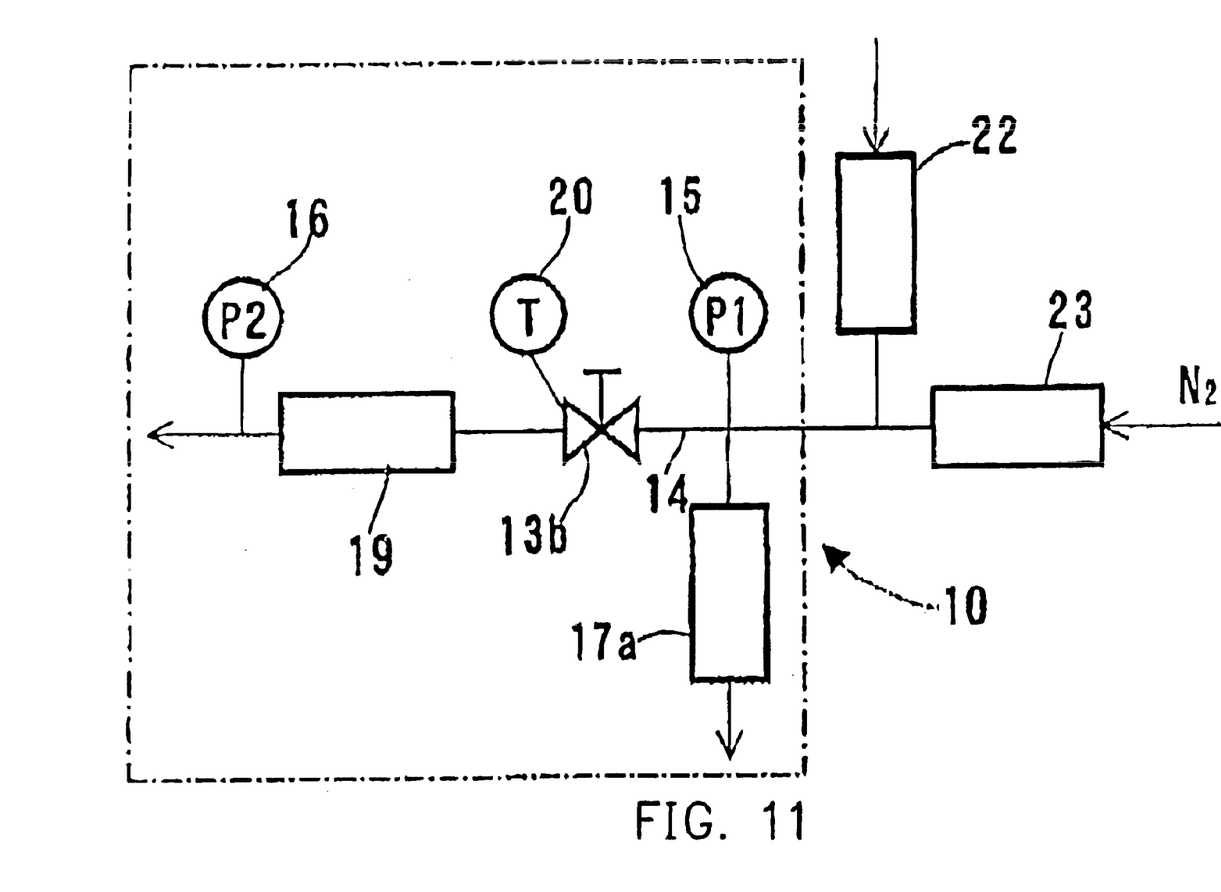
FIG. 11 illustrates the configuration of the experimental apparatus used in Example 2.

The experimental apparatus illustrated in FIG. 11 is used in this example. The apparatus is based on the apparatus used in Example 1, further including the parts described below. An upstream-side pressure gauge 15 is designed to measure the pressure at the upstream of the needle valve 13b. A downstream-side pressure gauge 16 is disposed at the downstream of the flow meter 19 to measure the pressure at the downstream the needle valve 13b. A temperature measuring device 20 capable of measuring the temperature of the needle valve 13b is also disposed in the apparatus.

Figure 12:
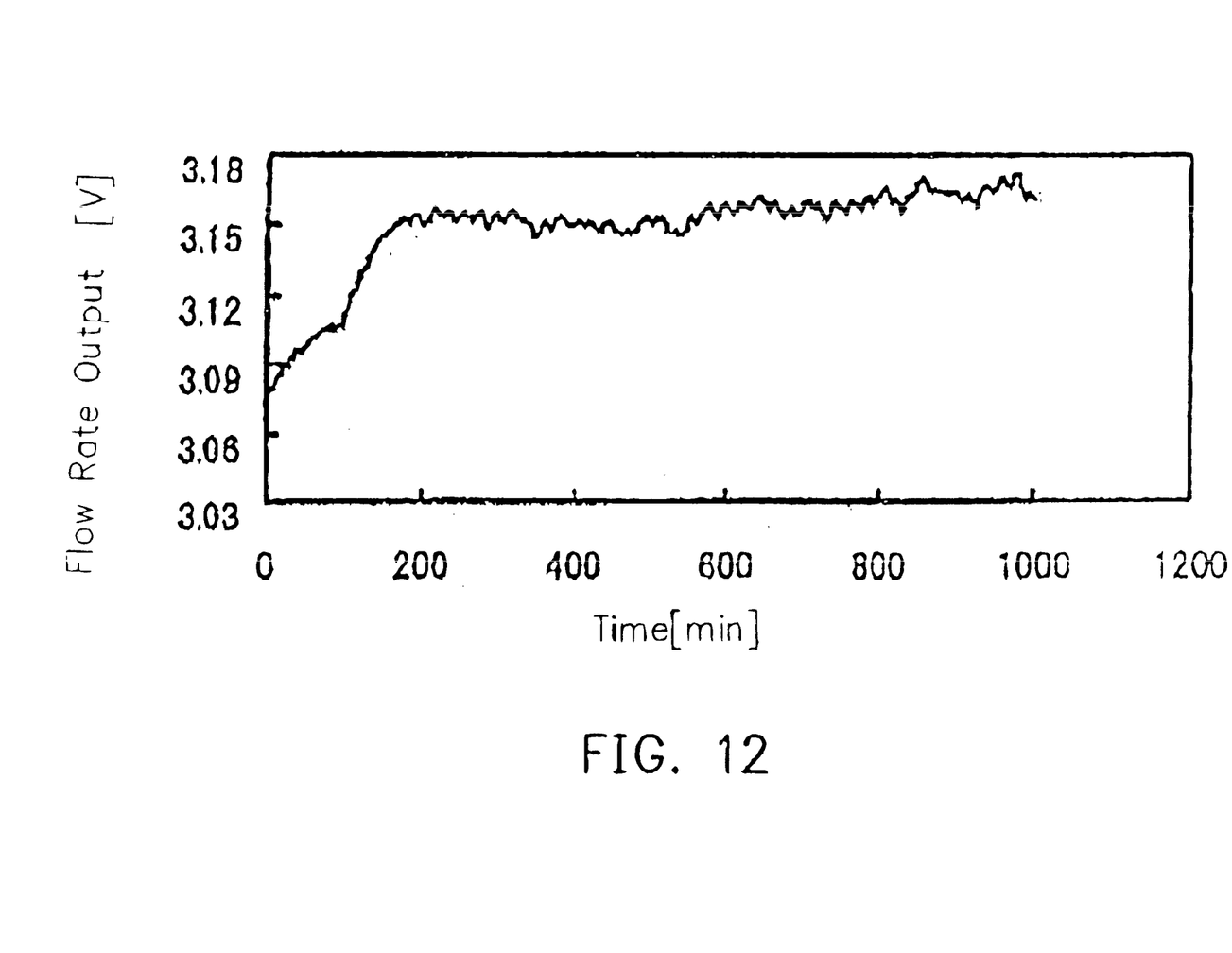
FIG. 12 plots the flow rate output when 100% pure nitrogen is supplied continuously.
Figure 13:
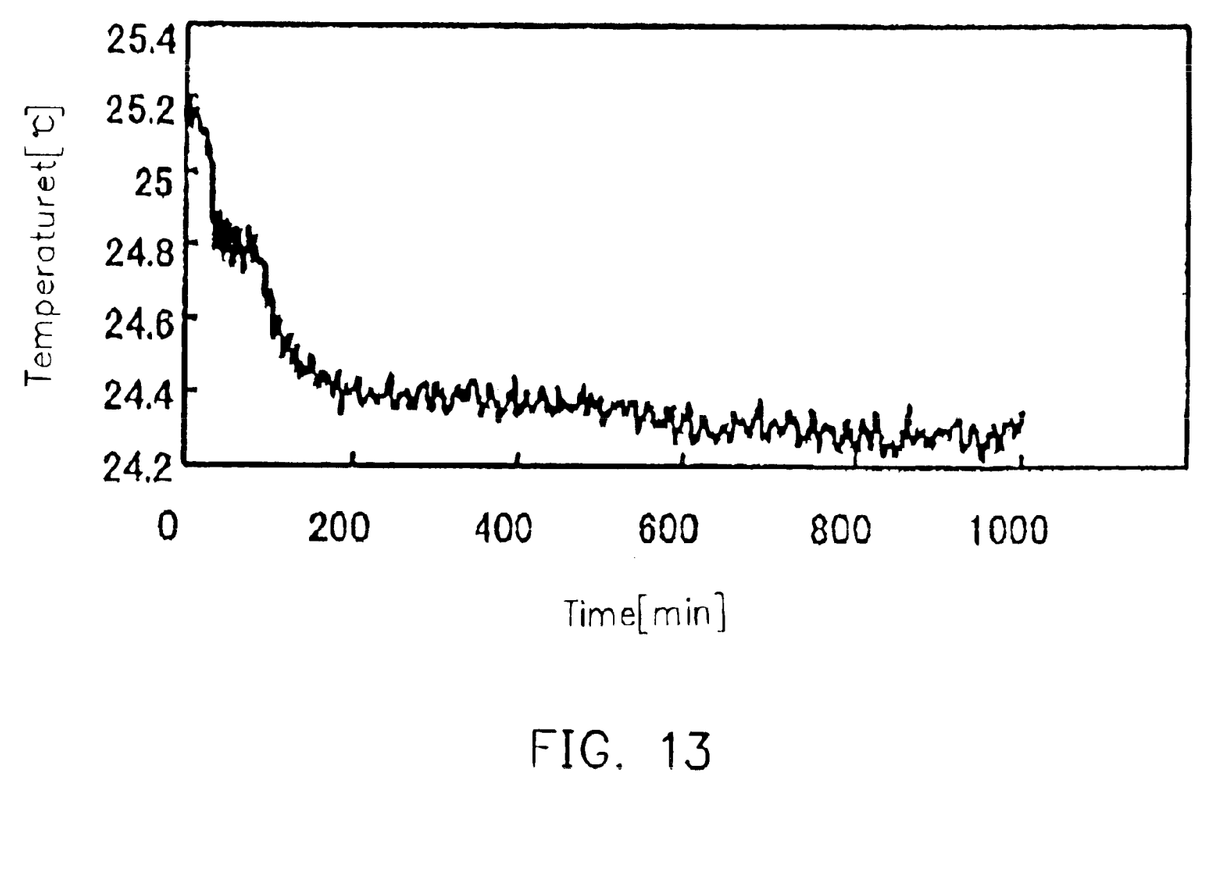
FIG. 13 plots the temperature of the needle valve when 100% pure nitrogen is supplied continuously.

The pressure difference between the upstream and the downstream of the needle valve 13b is maintained to be 45 kPa and a nitrogen gas of 100% purity is supplied continuously for 16 hours, while the flow rate output measured by using the flow meter 19 are shown in FIG. 12. Moreover, the temperature variation of the needle valve 13b measured with the temperature measuring device 20 is shown in FIG. 13, and the correlation between the temperature and the flow rate output is exhibited in FIG. 14.

Figure 14:
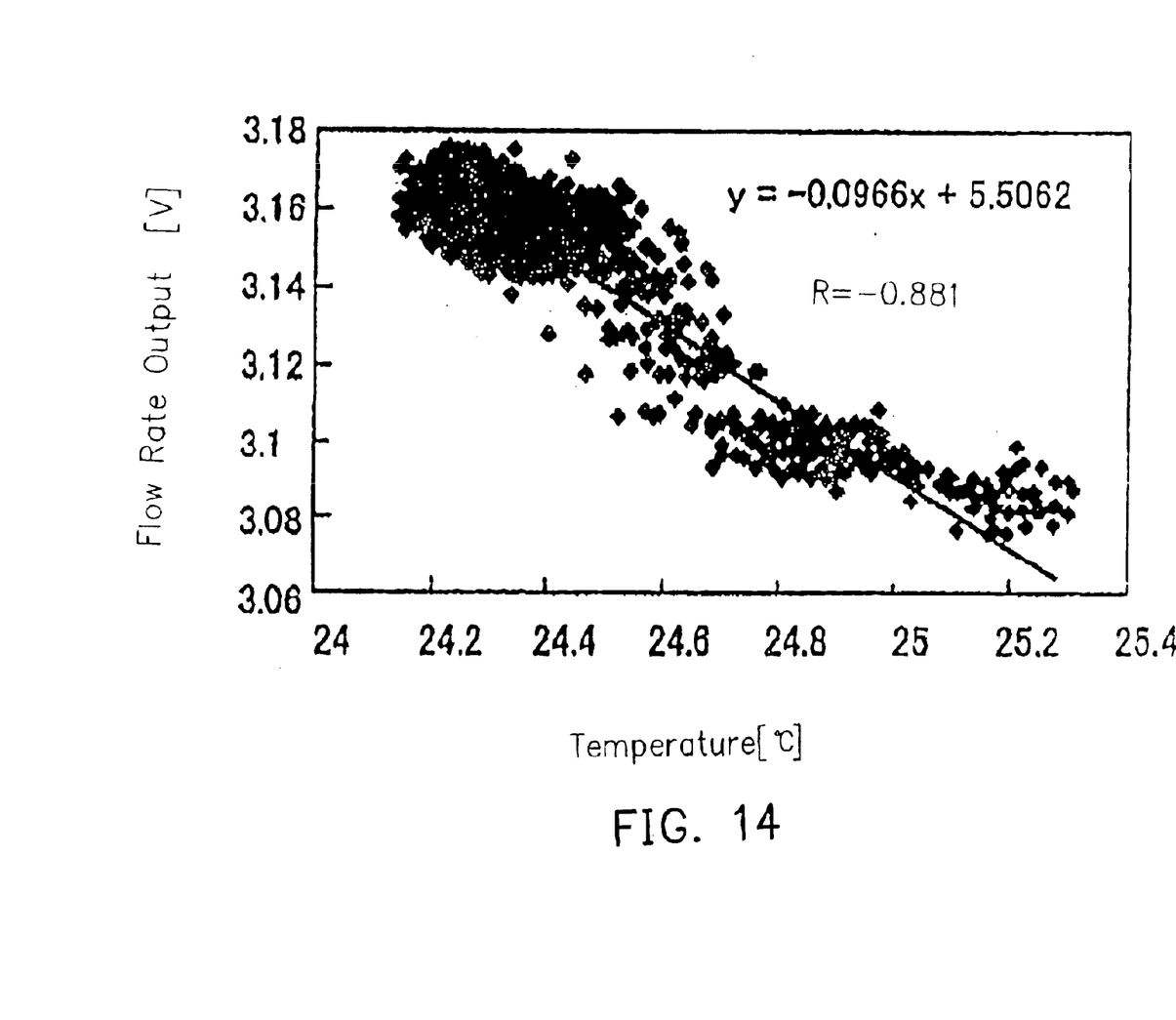
FIG. 14 exhibits the correlation between the temperature and the flow rate output.
Figure 15:
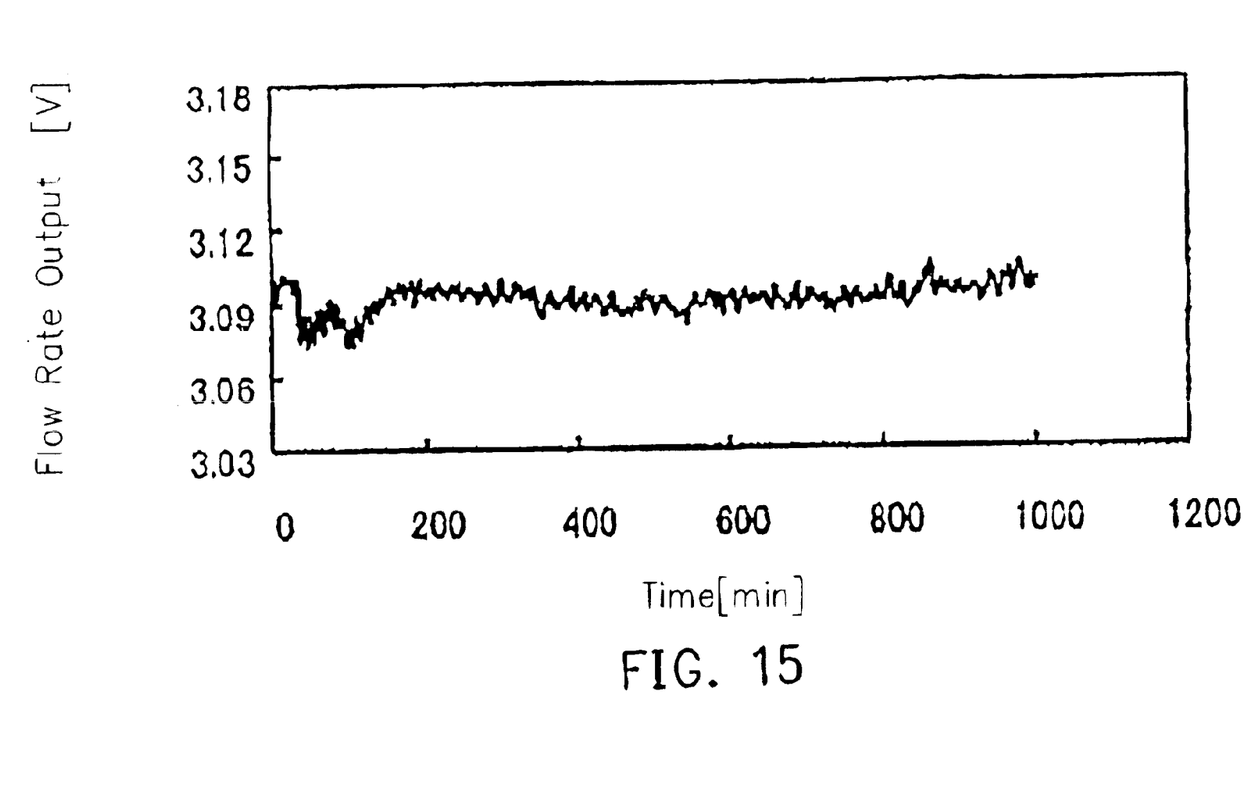
FIG. 15 plots the corrected flow rate output after the temperature-related correction.

As shown in FIG. 14, the flow rate output is negatively correlated to the temperature and the slope of the line is calculated to be −0.881. The slope is multiplied with a temperature difference based on 25° C. and then added onto the flow rate output just measured to carry out a temperature correction. The results are shown in FIG. 15.

EXAMPLE 3

Figure 16:
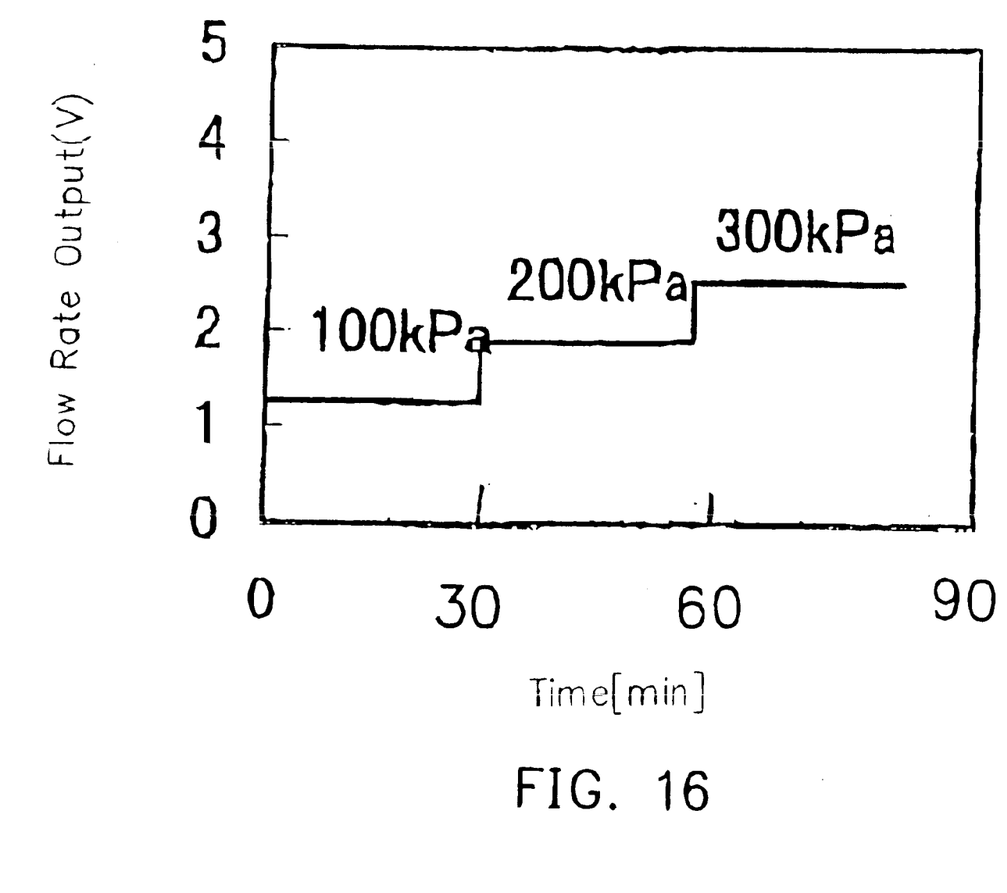
FIG. 16 plots the flow rate output with the pressure difference in Example 3.
Figure 17:
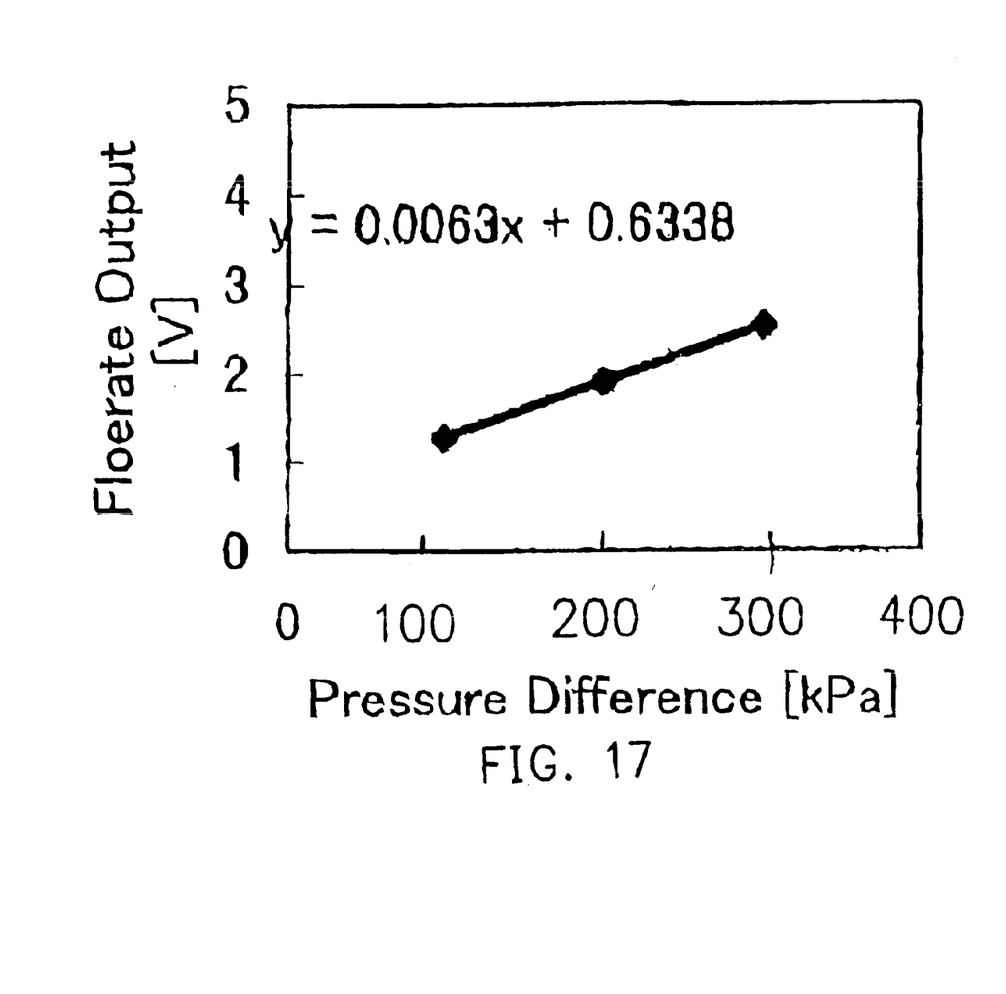
FIG. 17 plots the flow rate output with the pressure differences being varied with time.
Figure 18:
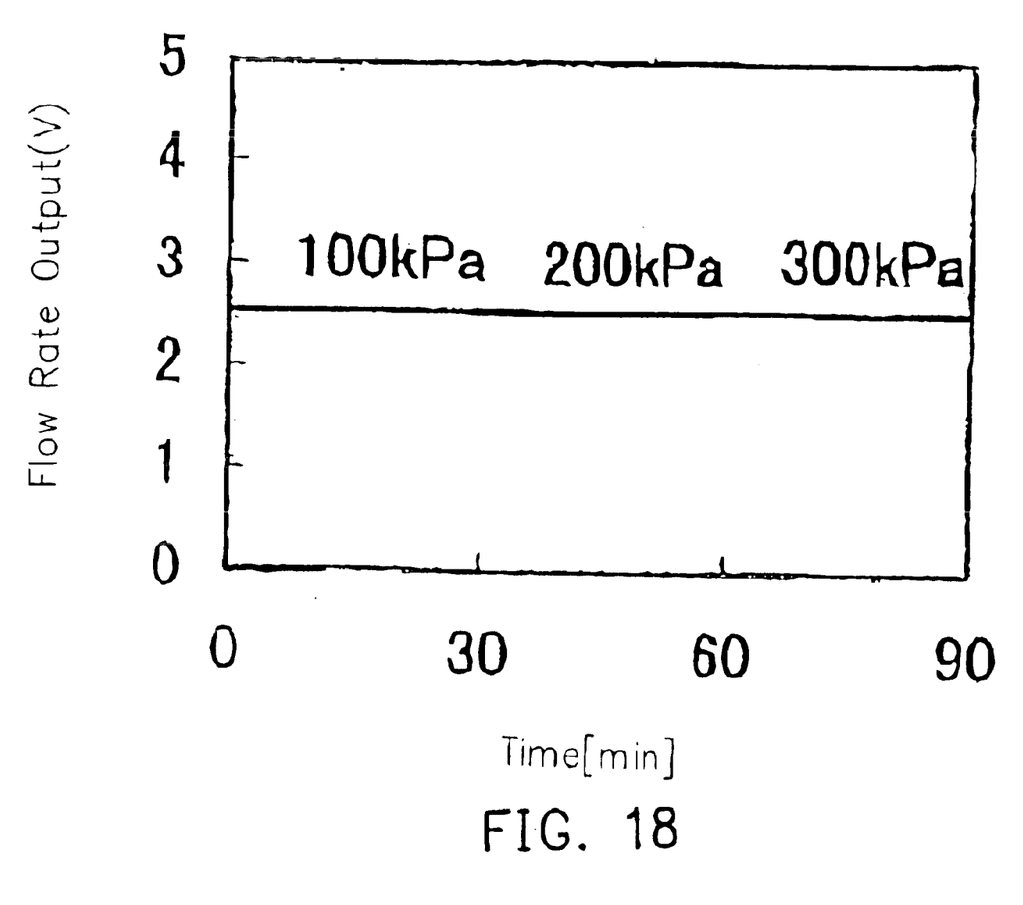
FIG. 18 plots the corrected flow rate output after the pressure-related correction.

The apparatus used in this example is the same as that in Example 2. The temperature of the needle valve 13b is maintained to be 25° C. and argon gas of 100% purity is supplied, while the pressure difference between the upstream and the downstream of the needle valve 13b is set as 100 kPa, 200 kPa and 300 kPa each for 30 minutes. FIG. 16 plots the flow rate output with the pressure differences being varied with time. Meanwhile, the flow rate output is plotted with the pressure difference in FIG. 17. As shown in FIG. 17, the flow rate output is positively correlated to the pressure difference and the slope of the line is calculated to be 3.73. The slope is multiplied with a pressure difference based on 300 kPa and then added onto the flow rate output just measured to carry out a pressure correction. The results are shown in FIG. 18.

In summary, by using the method and the apparatus of this invention, the concentrations of the components of a fluid can be determined continuously and accurately without mixing the other components. Moreover, this invention can be used to detect unknown impurities that are mixed into a pure fluid or a mixture fluid in real time and, if combined with a separating column, can be used to analyze the components qualitatively.

It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims and their equivalents.

What is claimed is:

1. A method for measuring concentrations of components of a two-component fluid, comprising:

conducting the two-component fluid through a measuring tube having a small aperture with a constant diameter in a fluid flow path, and a pressure difference of the two-component fluid between an upstream and a downstream of the small aperture is controlled to be constant; and measuring a flow rate at the downstream of the small aperture by using a flow meter of thermal-conductivity type to determine the density of the two-component fluid and determine the concentrations of the components of the two-component fluid based on the density, wherein one component of the two-component fluid is an IR-inactive gas selected from the group consisting of $N_2$, $O_2$, He, Ar, Kr and Xe.

2. The method of claim 1, wherein at least one of a first temperature of the fluid sample, a second temperature of the measuring tube and a third temperature of a circumstance of the measuring tube is measured for correcting the concentrations of the components.

3. The method of claim 1, wherein at least one of a first temperature of the fluid sample, a second temperature of the measuring tube and a third temperature of a circumstance of the measuring tube is controlled to be constant.

4. An apparatus for measuring concentrations of components of a two-component fluid, comprising:

a measuring tube having a small aperture with a constant diameter in a fluid flow path that allows the two-component fluid flowing through it;

a differential pressure controller for controlling a pressure difference between an upstream and a downstream of the small aperture to be constant;

a flow meter of thermal conductivity type, used for measuring a flow rate at the downstream of the small aperture; and a calculating device for calculating a density of the two-component fluid from the pressure difference and the flow rate being measured and calculating the concentrations of the components of the two-component fluid from the density, wherein one component of the two-component fluid is an IR-inactive gas selected from the group consisting of $N_2$, $O_2$, He, Ar, Kr and Xe.

5. The apparatus of claim 4, further comprising a temperature measuring device for measuring at least one of a first temperature of the measuring tube and a second temperature of a circumstance of the measuring tube, wherein the calculating device is capable of correcting the concentrations of the components based on the temperature being measured.

6. The apparatus of claim 4, further comprising a temperature controller for controlling at least one of a first temperature of the measuring tube and a second temperature of a circumstance of the measuring tube to be constant.

* * * * *